United States Patent [19]

Harrison et al.

[11] Patent Number: 5,112,821
[45] Date of Patent: May 12, 1992

[54] EXCITATORY AMINO ACID ANTAGONISTS WHICH ARE CERTAIN THIENOPYRIDINES

[75] Inventors: Boyd L. Harrison; Bruce M. Baron, Cincinnati, Ohio

[73] Assignee: Merrell Dow Pharmaceuticals Inc., Cincinnati, Ohio

[21] Appl. No.: 654,997

[22] Filed: Feb. 14, 1991

Related U.S. Application Data

[60] Division of Ser. No. 496,748, Mar. 21, 1990, Pat. No. 5,026,700, which is a continuation-in-part of Ser. No. 352,423, May 16, 1989, abandoned.

[51] Int. Cl.⁵ .................. A61K 31/435; C07D 495/04
[52] U.S. Cl. .................. 514/233.8; 514/301; 544/127; 546/114
[58] Field of Search ............ 546/114; 514/301, 233.8; 544/127

[56] References Cited

PUBLICATIONS

Barker et al., J. Chem. Res., Synop. p. 405 (1980).

Primary Examiner—Bernard Dentz
Attorney, Agent, or Firm—J. Michael Dixon

[57] ABSTRACT

The present invention is directed to a new class of excitatory amino acid antagonists.

8 Claims, No Drawings

EXCITATORY AMINO ACID ANTAGONISTS WHICH ARE CERTAIN THIENOPYRIDINES

Cross-Reference to Related Application

This is a divisional of application Ser. No. 07/496,748, filed Mar. 21, 1990 now U.S. Pat. No. 5026700, which is a continuation-in-part of application Ser. No. 07/352,423, filed May 16, 1989, now abandoned.

The present invention is directed to a new class of excitatory amino acid antagonists. Another aspect of the invention is directed to methods for the treatment of epilepsy, neurodegenerative diseases such as Huntington's disease, and for preventing ischemic/hypoxic damage to nervous tissues contained within the central nervous system.

In accordance with the present invention, a new class of excitatory amino acid antagonists which act at the NMDA receptor complex have been discovered. These compounds can be represented by the following formulae:

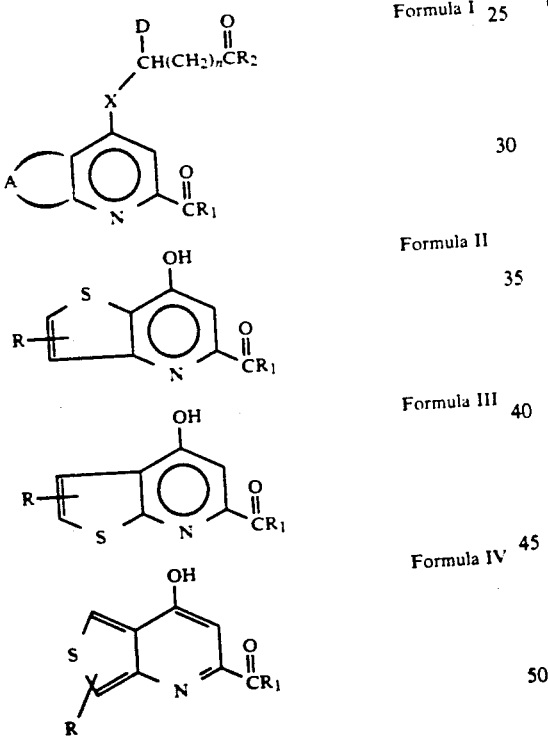

Formula I

Formula II

Formula III

Formula IV in which X is represented by a substituent selected from the group consisting of O, S, or NH; n is represented by an integer from 0 to 6; $R_1$ and $R_2$ are each independently represented by a substituent selected from the group consisting of $-NR_3R_4$, $-OH$, $-OR_5$, and $-OCH_2OCOR_6$ and, $-O-(CH_2)_p NR_7R_8$ in which p is an integer from 1-4; $R_3$ and $R_4$ are each independently represented by hydrogen or a $C_{1-6}$ alkyl; $R_5$ and $R_6$ are each independently represented by a $C_{1-6}$ alkyl, a phenyl ring, a substituted phenyl ring, or an alkylphenyl substituent in which the phenyl ring may be optionally substituted; $R_7$ and $R_8$ are independently represented by a $C_{1-6}$ alkyl or together with the adjacent nitrogen atom for a piperidino, morpholino, or pyrrolidinyl group; D is represented by hydrogen or a $C_{1-3}$ alkyl; and A is represented by:

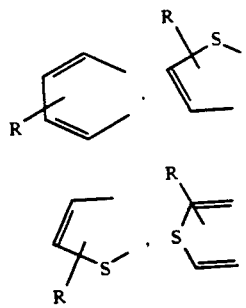

R is represented by a substituent selected from the group consisting of hydrogen, OH, halogen, CN, $NO_2$, $C_{1-6}$ alkyl, $C_{1-6}$ alkoxy, $OCF_3$, $CF_3$, $COOR_3$, and $CONR_3R_4$ in which $R_3$ and $R_4$ are each independently as defined above; the pharmaceutically acceptable acid addition salts thereof, and the pharmaceutically acceptable basic addition salts thereof.

As used in this application:

a) the term "halogen" refers to a fluorine, chlorine, or bromine atom;

b) the terms "lower alkyl group and $C_{1-6}$ alkyl" refer to a branched or straight chained alkyl group containing from 1-6 carbon atoms, such as methyl, ethyl, n-propyl, isopropyl, n-butyl, isobutyl, n-pentyl, n-hexyl, etc;

c) the terms "lower alkoxy group and $C_{1-6}$ alkoxy" refer to a straight or branched alkoxy group containing from 1-6 carbon atoms, such as methoxy, ethoxy, n-propoxy, isopropoxy, n-butoxy, isobutoxy, n-pentoxy, n-hexoxy, etc.;

d) the term "substituted phenyl ring" refers to a phenyl ($C_6H_5$) which is substituted with up to 3 substituents, each substituent is independently selected from the group consisting of halogens, $C_{1-6}$ alkyl, $C_{1-6}$ alkoxy, $CF_3$, $OCF_3$, OH, CN, $NO_2$, $COOR_3$, and $CONR_3R_4$ in which $R_3$ and $R_4$ are represented by hydrogen or a $C_{1-6}$ alkyl. These substituents may be the same or different and may be located at any of the ortho, meta, or para positions.

e) the term "alkylphenyl substituent" refers to the following structure $-(CH_2)_m-C_6H_5$, in which m is an integer from 1-3. This phenyl ring may be substituted in the manner described immediately above.

f) the term "$C_{1-3}$ alkyl" refers to a straight or branched alkyl group containing from 1-3 carbon atoms such as methyl, ethyl, n-propyl, or isopropyl.

The expression "pharmaceutically acceptable addition salts" is intended to apply to any non-toxic organic or inorganic acid addition salt of the base compounds represented by Formulae I-IV or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formulae I-IV or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

Some of the compounds of Formulae I-IV exist as optical isomers. Any reference in this application to one of the compounds represented by Formulae I-IV is meant to encompass either a specific optical isomer or a mixture of optical isomers. The specific optical isomers can be separated and recovered by techniques known in the art such as chromatography on chiral stationary phases or resolution via chiral salt formation and subsequent separation by selective crystallization.

The compounds of Formulae II, III, and IV may exist in the following tautomeric forms:

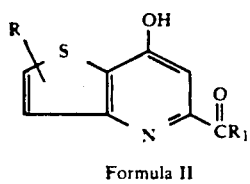
Formula II

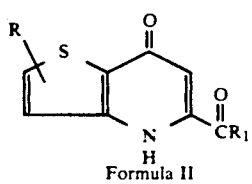
Formula II

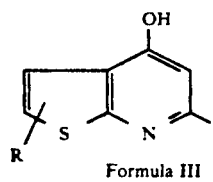
Formula III

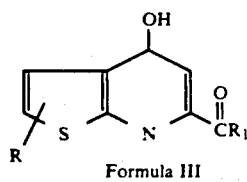
Formula III

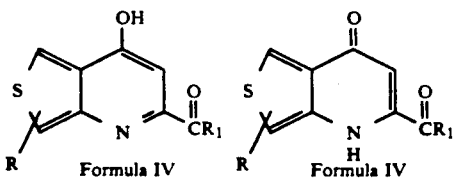
Formula IV

Formula IV

Any reference to the compounds of Formulae II, III, or IV should be considered as encompassing either of the tautomers.

In the compounds of Formula I, A can be represented by a phenyl ring bearing the substituent R. When R is other than a hydrogen atom, there can be up to 3 such substituents occurring on the indicated phenyl ring. These substituents can be the same or can different. These substituents can e located at any of the ortho, meta, or para positions. Likewise in the compounds of Formulae I-IV, $R_5$ and $R_6$ can be represented by either substituted phenyl rings or an alkylphenyl substituent in which the phenyl ring is substituted. These substituted phenyl rings may also be substituted with up to 3 substituents. These substituents may be the same or different and may be located at any of the meta, para, or ortho positions.

The thiophene derivatives of Formulae I-IV may contain substituents on their thiophene ring as represented by R. There may be up to 2 substituents appearing on the thiophene ring and these substituents may be the same or different. These substituents may appear at any of the free positions of the thiophene ring other than the position bearing the S atom. As used in this application, the term "free position" refers to a carbon atom in a cyclic structure that is substituted with only a hydrogen atom.

Illustrative examples of compounds encompassed by the present invention include:
a) 4-Carboxymethyloxy-2-quinolinecarboxylic acid
b) 4-Carboxymethyloxy-6-methoxy-2-quinolinecarboxylic acid
c) 4-Carboxymethyloxy-6-chloro-2-quinolinecarboxylic acid
d) 4-Carboxymethyloxy-7-chloro-2-quinolinecarboxylinc acid
e) n-Propyl 4-(n-propyloxycarbonyl)methyloxy-2-quinoline-carboxylate
f) 4-(3-Carboxypropyloxy)-2-quinolinecarboxylic acid
g) 4-(2-Carboxyethyloxy)-2-quinolinecarboxylic acid
h) 4-Carboxymethylamino-2-quinolinecarboxylic acid
i) 4-Carboxymethylthio-2-quinolinecarboxylic acid
j) 4-(2-Carboxyethylthio)quinoline-2-carboxylic acid
k) 4-Carboxymethyloxy-5,7-dichloro-2-quinolinecarboxylic acid
l) Methyl 4-methoxycarbonylmethyloxy-7-cyano-2-quinoline-carboxylate
m) 4-Carcboxymethyloxy-5-cyano-2-quinolinecarboxylic acid
n) 7-Hydroxythieno[3,2-b]pyridine-5-carboxylic acid
o) 4-Hydroxythieno[2,3-b]pyridine-6-carboxylic acid
p) Dimethyl 7-hydroxythieno[3,4-b]pyridine-3,5-dicarboxylate
q) 7-Hydroxythieno[3,4-b]pyridine-5-carboxylic acid
r) 7-Carboxymethyloxythieno[3,2-b]pyridine-5-carboxylic acid
s) 4-Carboxymethyloxythieno[2,3-b]pyridine-6-carboxylic acid
t) 4-Carboxymethyloxy-5-chloro-2-quinolinecarboxylic acid
u) 4-Carboxymethyloxy-7-methoxy-2-quinolinecarboxylic acid
v) 4-Carboxymethyloxy-8-fluoro-2-quinolinecarboxylic acid
w) 4-Carboxymethyloxy-8-chloro-2-quinolinecarboxylic acid
x) 4-Carboxymethyloxy-5,7-difluoro-2-quinolinecarboxylic acid
y) 7-Carboxymethyloxythieno[3,4-b]pyridine-3,5-dicarboxylic acid
z) 4-Carboxamidomethyloxy-2-quinolinecarboxamide
aa) Pivaloyloxymethyl 4-carboxymethyloxy-5,6-dichloro-2-quinolinecarboxylate
bb) 4-Carboxymethyloxy-7-fluoro-2-quinolinecarboxylic acid
cc) 4-Carboxymethylamine-5,7-dichloro-2-quinolinecarboxylic acid
dd) 2-(Diethylamino)ethyl 5,7-dichloro-4-[2-(diethylamino)-ethyloxycarbonyl]methylamino-2-quinolinecarboxylate
ee) 2-(Dimethylamino) ethyl 5,7-dichloro-4-[2-(dimethyl-amino)ethyloxycarbonyl]methyloxy-2-quinolinecarboxylate ff) 4-Carboxymethyloxy-6,7,-trifluoromethyl-2-quinoline-carboxylic acid gg) 4-Carboxymethyloxy-6,7-dichloro-2-quinolinecarboxylic acid The preferred compounds of the present invention are those of Formula I in which X is represented by O, or NH and A forms a phenyl ring which is either unsubstituted, monosubstituted at the 7-position with a chlorine atom, or is disubstituted with chlorine atoms at positions 5 and 7. It is preferred for $R_1$ and $R_2$ to be represented by either a hydroxyl or an ester function.

The compounds of Formula I can be prepared by methods which are analogously known in the art. For example those compounds of Formula I in which X is represented by either O or S and n is represented by the integer 0 or 2-6, can be produced by conducting an alkylation reaction between a condensed carbocyclic or heterocyclic 4-substituted pyridine 2-carboxylate derivative (hereinafter "annulated pyridine") as described by Formula V and a 4-substituted alkanoic acid (hereinafter "ω-alkanoic acid") derivative as described by Formula VI below:

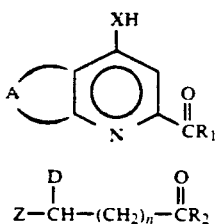

Formula V

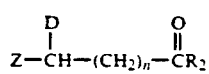

Formula VI

In Formula V, X is represented by O or S, and A, and $R_1$ are as defined in Formula I. It is preferred that the non-reacting substituents of the annulated pyridine of Formula V, correspond to those appearing in the final product with the exception of $R_1$. If $R_1$ is to be represented by —OH in the final product, then it should be protected during the alkylation with a suitable protecting group such as a $C_{1-6}$ alkyl. For those compounds in which $R_1$ is to be represented by either an ester derivative or an amide derivative, then the desired amide or ester can be added to the core structure of Formula V prior to the alkylation reaction or it can be added to the core structure of Formula I after the alkylation reaction has been completed utilizing techniques well known in the art.

In Formula VI, Z is a leaving group such as a halogen, —OSO$_2$CH$_3$, or —O—SO$_2$—C$_6$H$_5$—CH$_3$ and $R_2$, D, and n are as defined in Formula I. It is also preferred that the non-reacting substituents of the ω-alkanoic acid derivative other than $R_2$ correspond to those appearing in the final product. If $R_2$ is to be represented by OH in the final product, then it should be protected during the alkylation with a suitable protecting group such as a $C_{1-6}$ alkyl. For those compounds in which $R_2$ is to be represented by either an ester or amide derivative, an w-alkanoic acid derivative may be utilized in which $R_2$ is represented by the desired ester or amide derivative or the desired ester or amide derivative can be added to the core structure of Formula I upon completion of the alkylation reaction by techniques well known in the art.

As noted above, ester and amide derivatives can be added to the $R_1$ and $R_2$ positions of the core structure of Formula I by methods well known in the art. One suitable esterification method for the compounds of Formula I is to contact a compound of Formula I in which $R_1$ and $R_2$ are represented by OH with a base such as diethylisopropylamine, in a polar inert solvent such as dimethylformamide, dimethylsulfoxide, acetonitrile, acetone or tetrahydrofuran, thereby forming a bis carboxylate salt. The bis carboxylate salt is then contacted with 2 to 5 equivalents, preferably about 2.5 equivalents, of an alkylhalide corresponding to the desired ester, and allowed to react at a temperature of about 25° C. for a period of time ranging from 16-24 hours. The reaction mixture is then quenched with dilute aqueous acid and extractive work-up as is known in the art affords the diester compounds of Formula I, which can be purified by standard methods such as chromatography, recrystallization, or distillation.

Amides can also be easily added to the compounds of Formula I by taking a compound of Formula I in which $R_1$ and $R_2$ are each represented by ester functions and contacting it with an excess of ammonia or a mono- or dialkylamine at a temperature of from 0°-100° C. for a period of time ranging from 1-48 hours in an alcoholic solvent such as methanol or ethanol. The resulting amide derivatives of Formula I can then be isolated and purified by techniques known in the art.

Another method for producing amides or esters comprises contacting a compound of Formula I in which $R_1$ and $R_2$ are represented by —OH with a halogenating agent such as thionyl chloride, oxalyl chloride, phosphorus oxychloride, phosphorus pentachloride, etc. The resulting diacid halides are then contacted with an excess of ammonia, monoalkyl-amines, dialkylamines, aliphatic alcohols, aromatic alcohols or a dialkylamino alkyl alcohol such as dimethylaminoethanol, diethylaminoethanol, optionally in the presence of a base such as a tertiary alkylamine, in an inert solvent such as ether, dioxane, tetrahydrofuran, etc. at a temperature of from 0°-25° C. for a period of time ranging from 5-16 hours. The resulting amides or esters can be isolated and purified by methods known in the art.

The alkylation reaction between the annulated pyridine of Formula V and the ω-alkanoic acid derivative of Formula VI is conducted according to techniques known in the art. Typically, the annulated pyridine of Formula V is first contacted with from about 1 to about 5 equivalents of a base and more preferably from about 1 to about 2.5 equivalents. The base and the annulated pyridine are stirred together at a temperature range of from about 0° C. to about 25° C. for a period of time ranging from about 5 minutes to about 60 minutes in a solvent. Suitable bases include alkali metal carbonates and bicarbonates such as potassium carbonate, alkali metal hydroxides such as sodium hydroxide, alkali metal hydrides such as sodium hydride, or tertiary alkylamines such as triethyl amine. Suitable solvents include diethyl ether, tetrahydrofuran, dimethylformamide, dimethylsulfoxide, sulfolane, N-methyl-2-pyrollidone, benzene, toluene, acetone, butanone, methanol, ethanol, water or mixtures of water and water miscible solvents. Dimethylformamide is typically utilized.

An approximately equimolar amount of the ω-alkanoic acid derivative of Formula VI is then added to the reaction mixture and the reactants are stirred together for a period of time ranging from about 2 to about 48 hours and more preferably from 5 to 24 hours. The alkylation reaction is conducted at a temperature range of from about -40° C. to about 100° C. and more preferably from 25° C. to 50° C.

The completed reaction is quenched into water, saturated ammonium chloride, or dilute aqueous acid. The product can then be recovered and purified by techniques well known in the art. For example the product can be recovered by either extraction with an organic solvent, or concentration and filtration of the resulting solid. The crude product can then be purified by chromatographic techniques such as silica gel chromatography or by recrystallization from a solvent system such as ethyl acetate/hexane or methanol/water.

The ω-alkanoic acid derivatives of Formula VI are known in the art as are methods for their preparation. Many of these derivatives are commercially available.

Methods for producing the annulated pyridines of Formula V are known in the art. The starting materials for the annulated pyridines of Formula V in which X is either O or S, is an acetylinic dicarboxylic ester as described by Formula VII and an aromatic amino compound as described by Formula VIII:

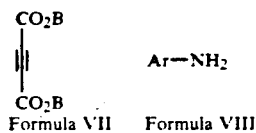

In Formula VII, B is represented by an alkyl residue such as methyl or ethyl. In Formula VIII, Ar is represented by one of the following aromatic rings:

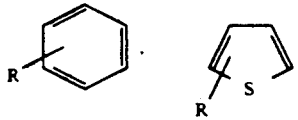

As is apparent to those skilled in he art, the particular aromatic amino compound that is utilized should be structurally analogous to the residue which is represented by A in the desired compound of Formula I.

A Michael condensation is conducted with the acetylinic dicarboxylic ester of Formula VII and the aromatic amine of Formula VIII thereby producing a Michael adduct as described by Formula IX in which Ar and B are as defined above:

The Michael condensation is conducted according to techniques known in the art. Typically, one equivalent of the aromatic amine of Formula VIII is contacted with about 1 to about 2 equivalents, and more preferably from about 1.1 to about 1.5 equivalents of the acetylinic dicarboxylic ester of Formula VII. The reaction is typically conducted at a temperature range of from about 25° C. to about 200° C., and more preferably from about 40° C. to about 110° C. for a period of time ranging from about 2 to about 48 hours and more preferably from about 5 to about 24 hours. The reaction can be conducted either neat or in a solvent such as methanol, ethanol, benzene, toluene, chloroform, tetrahydrofuran. Methanol is preferred.

After the reaction is completed, the solvent is evaporated and the resulting oil can be utilized directly in the next step of the synthesis. If desired, the crude amino adduct can be purified by conventional techniques known in the art such as silica gel chromatography.

The next step in the synthesis of the annulated pyridines of Formula V is the cyclization of the Michael adduct of Formula IX thereby producing an annulated pyridine of Formula V in which X is represented by O.

The cyclization is accomplished by heating the adduct of Formula IX to a temperature range of from about 150 to about 300° C., (preferably from 200°-270° C.) in a solvent such as diphenyl ether, nujol, or polyphosphoric acid for a period of time ranging from about 0.1 to about 3 hours and more preferably from 25 minutes to 60 minutes. The reaction mixture is then cooled to about 25° C. and the resulting precipitated product is collected by filtration. If desired, a hydrocarbon solvent such as hexane may be added to the reaction mixture to speed the precipitation of the solid. If a solid is not formed during this cooling period, then the bulk of the high boiling solvent is removed under vacuum and the product is then isolated by techniques known in the art. After the product is collected, it is washed in a hydrocarbon solvent and air dried. The crude annulated pyridine in which X is represented by O may be utilized in the alkylation reaction with the ω-alkanoic acid derivative or it may be utilized to produce an annulated pyridine of Formula V in which X is represented by S.

As is evident from structure IX, Michael adducts which would be formed from certain unsymmetrical aromatic amines could produce mixtures of positional isomers in the cyclization reaction which forms the annulated pyridines of Formula V. These mixtures may be separated by methods well known in the art such as fractional crystallization or column chromatography. For example, condensation of 3-chloroaniline with dimethyl acetylenedicarboxylate and subsequent cyclization of the obtained Michael adduct affords a mixture of methyl 5-chloro-4-hydroxy-2-quinolinecarboxylate and methyl 7-chloro-4-hydroxy-2-quinolinecarboxylate, which can be separated by fractional crystallization from acetic acid as outlined by Heindel, et al., J. Med. Chem., 11, p. 1218 (1968).

Alternatively mixtures of isomers which are not separated at the Formula V stage may be converted to mixtures of Formula I and then separated by methods known in the art such as fractional crystallization or column chromatography. For example, a mixture of methyl 5-cyano-4-hydroxy-2-quinolinecarboxylate and methyl 7-cyano-4-hydroxy-2-quinolinecarboxylate can be alkylated as described above with methyl bromoacetate and the resulting mixture of 5- and 7-cyano positional isomers of the product can be separated by flash column chromatography on silica gel using ethyl acetate/hexane as eluant.

The annulated pyridines of Formula V produced by the cyclization reaction can be optionally purified by techniques known in the art such as silica gel chromatography or recrystallization from a solvent such as methanol, methanol/water, or DMF/water prior to its conversion into one of the compounds of Formula I.

The annulated pyridines of Formula V in which X is represented by O can be utilized to produce the annulated pyridines of Formula V in which X is represented by S in the following manner. Typically about 1 equivalent of the annulated pyridine of Formula V in which X is represented by O will be contacted with about 0.5 to about 1.0 equivalents of a thiocarbonylating reagent, such as, for example, Lawesson's reagent, $P_2S_5$/pyridine, etc. The reactants are typically stirred together at a temperature range of from about 0° C. to about 110° C., and more preferably from about 25° C. to about 60° C., for a period of time ranging from about 0.5 hours to about 24 hours. The reaction is typically conducted in a dry solvent, typically an ether such as, dimethoxyethane or THF. After the reaction is completed, it is typically quenched in ice water and the product is recovered directly by filtration or by extraction with an organic solvent. The resulting organic phase is then separated, dried, and evaporated at reduced pressures, thereby producing the desired annulated pyridine in which X is represented by S. This crude product can be utilized or it can be further purified by techniques known in the art such as recrystallization or column chromatography.

The method disclosed above for synthesizing the annulated pyridines of Formula V, produces a compound in which $R_1$ will be represented by an alkoxy residue such as methoxy or ethoxy. This annulated pyridine may be utilized directly in the alkylation reaction with the ω-alkanoic acid derivative and the appropriate carboxylic acid derivative may be added after the completion of the alkylation reaction. Alternatively, the methyl or ethyl residue may be removed by conducting a basic hydrolysis and the appropriate carboxylic acid derivative may be added to the annulated pyridine by techniques known in the art prior to conducting the alkylation reaction.

The compounds of the present invention which can be described by Formulae II, III, and IV can also be produced utilizing the same synthetic method as that taught for producing the annulated pyridines of Formula V. As is readily apparent, those compounds of Formula V in which X is O and A is a thiophene residue are the subject of Formulae II, III, and IV. Thus the description of the appropriate starting materials, reaction conditions, and means of purifications discussed immediately above is equally applicable to either the annulated pyridines of Formula V or the compounds of Formulae II, III, or IV.

The compounds of Formula I in which X is represented by O and n is represented by 1 can be made in the following manner. Initially an annulated pyridine as previously described by Formula V in which X is represented by O, is subjected to an addition reaction with a propargylic ester as described by Formula X in which B is represented by a protecting group such as a $C_{1-6}$ alkyl or a phenyl ring and D is as in Formula I:

Formula X

This addition reaction produces an intermediate as described by Formula XI:

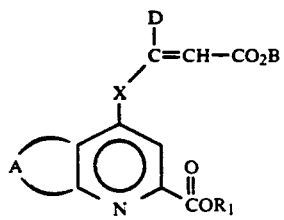

Formula XI in which X is O, $R_1$, D, and A are as defined in Formula I and B is as described above. The intermediate of Formula XI is then subjected to a reductive hydrogenation thereby producing the desired compound of Formula I.

As is apparent to those skilled in the art, it is preferred that the nonreacting substituents of the annulated pyridine correspond to those appearing in the desired product. When $R_1$ is to be represented by either an ester, or amide derivative, then the appropriate carboxylic derivative can be placed on the annulated pyridine starting material or it can be added after the hydrogenation reaction is completed. Likewise, if $R_1$ is to be represented by —OH in the final product, then it should be protected with a suitable protecting group such as a $C_{1-6}$ alkyl during the reaction with the propargylic ester. Likewise, if the protecting group of the propargylic ester is not identical to the $R_2$ substituent in the desired product, then the appropriate $R_2$ substituent can be added to the core structure of Formula I using methods known in the art after the hydrogenation reaction is completed.

The addition reaction between the annulated pyridine of Formula V and the propargylic ester of Formula X can be accomplished according to techniques known in the art. Typically the annulated pyridine is contacted with 1 to 2 equivalents of a base and from about 1 to about 2 equivalents of the propargylic ester of Formula X. The reactants are heated to a temperature range of from about 60° C. to about 90° C. for a period of time ranging from about 1 hour to about 48 hours. Suitable bases include trialkyl amines such as triethyl amine, alkali metal alcoholates such as sodium methoxide, alkali metal carbonates, and bicarbonates such as sodium bicarbonate and potassium carbonate. The reaction is also typically conducted in a solvent such as diethylether, tetrahydrofuran, dioxane, methanol, ethanol, tert-butanol, isopropanol, t-amyl alcohol, benzene, etc. Alcohols are currently preferred; t-butanol is most preferred.

Upon completion of the addition reaction, the product is typically recovered by evaporating the solvent under a vacuum. The resulting oil is typically redissolved in one of the non-water soluble solvents described above, or in a halogenated solvent such as $CHCl_3$ or $CH_2Cl_2$, and is then washed in succession with a dilute aqueous mineral acid, a dilute aqueous base, water, and a saturated solution of sodium chloride. The resulting organic layer is then dried over standard drying agents, and evaporated under a vacuum to afford the crude intermediate of Formula XI. This crude intermediate may be hydrogenated without further purification. If desired, it may be purified by either recrystallization or chromatography on silica gel.

The reductive hydrogenation of the intermediate of Formula XI is accomplished in the following manner. The intermediate is dissolved in an organic solvent such as a lower alkyl alcohol, acetic acid, ethyl acetate, or tetrahydrofuran and contacted with from 1-10 weight percent of a transition metal catalyst such as, for example, palladium on charcoal. The hydrogenation is conducted under 1-4 atmospheres, preferably 2-3 atmospheres, of $H_2$ gas at a temperature range of 20°-30° C. The reaction is stopped when one equivalent of hydrogen is consumed. The catalyst is removed by filtration and the desired compound of Formula I is recovered by techniques known in the art such as extraction. It can also be purified by techniques known in the art such as chromatography on silica gel or recrystallization from a solvent system such as ethylacetate/hexane.

Those compounds of Formula I in which X is represented by S and n is represented by 1 can be made in the following manner. Typically they are produced by carrying out an alkylation reaction between an annulated pyridine as previously described by Formula V in which X is represented by S and an acrylic acid derivative as described by Formula XII:

Formula XII in which $R_2$ and D are as defined in Formula I or $R_2$ is represented by a suitable protecting group such as a $C_{1-6}$ alkyl.

This alkylation reaction is conducted in a manner similar to the alkylation reaction between the annulated pyridine of Formula V and the ω-alkanoic acid derivative of Formula VI which was discussed above. As in that alkylation reaction, when $R_1$ and $R_2$ are to be represented by either amide or ester derivatives, these can be added to the core structure of Formula I by techniques well known in the art or the alkylation can be conducted with reactants having the appropriate $R_1$ and $R_2$ substituents. The desired compound of Formula I can be recovered and purified by methods similar to those taught above.

The compounds of Formula I in which X is represented by NH and n is the integer O or 2-6 can be produced utilizing techniques known in the art. For example they can be produced by conducting an alkylation reaction between a ω-alkanoic acid derivative as previously described by Formula VI and an activated annulated pyridine as described by Formula XIII:

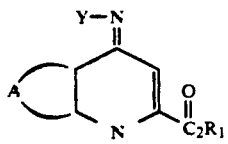

Formula XIII in which Y is represented by $-SO_2-C_6H_6$, $-SO_2-C_6H_5-CH_3$, $-SO_2-O-C_6H_5-Cl$, $-CO-CCl_3$, or $-CO-CF_3$ and both $R_1$ and A are as defined in Formula I.

The alkylation reaction between the activated annulated pyridine of Formula XIII and the ω-alkanoic acid derivative of Formula VI is conducted in a manner similar to that described for the alkylation reaction between the annulated pyridine of Formula V and the ω-alkanoic acid derivative of Formula VI. Thus the discussion concerning the proper criterion for the reactants, the proper reaction conditions as well as suitable methods of isolation, and purification of the product produced thereby are equally applicable to this reaction as well.

This alkylation reaction produces an intermediate which can be described by Formula XIV in which Y is as defined above and $R_1$, $R_2$, A, D, and n are as defined in Formula I:

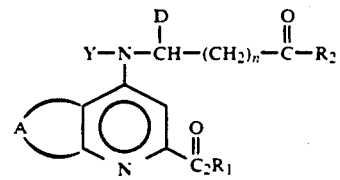

Formula XIV

The desired compound of Formula I can be produced from the intermediate of Formula XIV by subjecting the intermediate to a hydrolysis reaction thereby removing the activating group Y. This hydrolysis can be conducted utilizing techniques well known in the art. For example, the intermediate is typically contacted with from about 3 to about 10 equivalents of a strong mineral acid such as concentrated or 90% sulfuric acid. The intermediate is typically stirred in the presence of the acid for a period of time ranging from 0.5 hours to about 3 hours at a temperature range of from 0° C. to about 25° C. The hydrolysis can be conducted in neat acid. Upon completion of the hydrolysis, the desired compound of Formula I can be recovered by techniques well known in the art such as quenching into water and extraction with an organic solvent. It can also be purified by techniques known in the art such as recrystallization from a solvent system such as methanol/DMF, chromatography on silica gel, or ion-exchange chromatography.

If desired, the groups Y and $R_1$ and $R_2$ can be removed sequentially, that is, conditions can be found such that the group Y can be hydrolyzed as described but $R_1$ and $R_2$ are left intact. The ester function can then be removed as described earlier (hydrolysis methods known in the art). Conversely, $R_1$ and $R_2$ can be removed preferentially by methods known in the art, leaving the Y group intact which then can be removed as above.

The activated annulated pyridines of Formula XIII can be produced using techniques well known in the art. Typically an annulated pyridine as described by Formula V in which X is represented by O is contacted with an activated isocyanate of the formula:

in which Y is as defined above. The reactants are contacted in an inert solvent, preferably acetonitrile or propionitrile, at a temperature from 50°-150° C., preferably 70°-110° C. for a period of time ranging from 0.5-24 hours, and more preferably from 1-16 hours. The resulting activated annulated pyridine of Formula XIII can be isolated and purified by techniques known in the art.

Alternatively, the activated annulated pyridines of Formula XIII can be produced by contacting an annulated pyridine of Formula V in which X is represented by NH with an acylating agent such as trifuluroacetic anhydride or trichloroacetyl chloride. The resulting product can be isolated and purified by techniques known in the art.

The annulated pyridines of Formula V in which X is represented by NH are known in the art as are their methods of preparation. Wright, Synthesis, pg. 1058 (1984).

The annulated pyridines of Formula I in which X is represented by NH and n is represented by 1 can be produced by methods known in the art. An alkylation reaction is conducted between an annulated pyridine as previously described by Formula V in which X is represented by NH and an acrylic acid derivative as previously described by Formula XII. This alkylation produces the desired compound of Formula I in which X is represented by NH, n is 1, and D, $R_1$, $R_2$, and A are as defined in Formula I. The alkylation reaction can be conducted in a manner analogous to the alkylation reaction between the annulated pyridine of Formula V and the ω-alkanoic acid derivatives of Formula VI which was previously discussed. Likewise the compounds can be isolated and purified in the same manner as that taught above. As in the other reaction schemes, if either $R_1$ or $R_2$ is not the desired ester or amide derivative, then the appropriate ester or amide derivative can be added to the molecule using techniques well known in the art.

The compounds of Formulae I-IV are excitatory amino acid antagonists. They antagonize the effects which excitatory amino acids have upon the NMDA receptor complex. They preferentially bind to the strychnine-insensitive glycine binding site located on the NMDA receptor complex. They are useful in the treatment of a number of disease states.

Ischemia, hypoglycemia, and trauma have been shown to raise extracellular concentrations of glutamate and aspartate to potentially neurotoxic levels. These antagonists will be neuroprotective in these and potentially other syndromes characterized by elevated glutamate and or aspartate concentrations.

The compounds exhibit anti-convulsant properties and are useful in the treatment of epilepsy. They are useful in the treatment of grand mal seizures, petit mal seizures, psychomotor seizures, and autonomic seizures. One method of demonstrating their anti-epileptic properties is by the compounds ability to inhibit audiogenic convulsions in DBA/2 mice. This test can be conducted in the following manner.

Typically one group of from 6-8 male DBA/2J audiogenic susceptible mice are administered from about 0.01 μg to about 100 μg of the test compound. The test compound is administered intracerebrally into the lateral ventricle of the brain. A second group of mice are administered an equal volume of a saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

The compounds of Formulae I-IV are useful for preventing or minimizing the damage which nervous tissues contained within the CNS suffer upon exposure to either ischemic, hypoxic, or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, reduction of neuronal damage following trauma to the brain or spinal cord, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. It was discovered that anxiolytic agents block these vocalizations. The testing methods have been described by Gardner, C.R., Distress vocalization in rat pups: a simple screening method for anxiolytic drugs. *J. Pharmacol. Methods*, 14:181-187 (1885) and Insel et al. Rat pup ultrasonic isolation calls: Possible mediation by the benzodiapine receptor complex. *Pharmacol. Biochem. Behav*., 24: 1263-1267 (1986).

The compounds also exhibit an analgesic effect and are useful in controlling pain.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

As used in this application:
a) the term patient refers to warm blooded animals such as, for example, guinea pigs, mice, rats, cats, rabbits, dogs, monkeys, chimpanzees, and humans;
b) the term treat refers to the ability of the compounds to either relieve, alleviate, or slow the progression of the patient's disease;
c) the term neurodegeneration refers to a progressive death and disappearance of a population of nerve cells occurring in a manner characteristic of a particular disease state and leading to brain damage.

The compounds may also be admixed with any inert carrier and utilized in laboratory assays in order to determine the concentration of the compounds within the serum, urine. etc., of the patient as is known in the art.

Neurodegenerative diseases are typically associated with 10 loss of NMDA receptors. Thus, the compounds of Formula I-IV may be utilized in diagnostic procedures to aid physicians with the diagnosis of neurodegenerative diseases. The compounds may be labeled with isotopic agents by techniques known in the art and utilized as imaging agents. They may then be administered to a patient in order to determine whether the patient is exhibiting a decreased number of NMDA receptors and the rate at which that loss is occurring.

The following examples are presented in order to further illustrate the invention. They should not be construed as limiting the invention in any manner.

EXAMPLE 1

The purpose of this example is to demonstrate a method for the preparation of the annulated pyridine intermediates of Formula V. Using this same methodology, but substituting the appropriate starting materials, the compounds of Formulae II, III, and IV can also be produced by the same techniques.

Purified aniline (15.0 g, 0.16 mole) was reacted with dimethyl acetylenedicarboxylate (19.8 ml, 0.15 mole) in 400 ml methanol according to the procedure of Heindel, et al., J. Het. Chem. 1966, 3, 222. The reaction was refluxed for 18 hours, then worked up by evaporating the solvent, dissolving the residue in ether, and washing consecutively with 0.5 N HCl, H$_2$O, and sat. NaCl. The organic layer was dried over MgSO$_4$ and concentrated. The crude product was purified by flash chromatography on silica gel in 80/20 hexane/EtOAc which yielded 29.14 g of the Michael Adduct, dimethyl anilinofumarate as a light yellow oil.

Some of the Michael Adduct, dimethyl anilino-fumarate produced as above, (15.0 g, 0.06 mole) was dissolved in diphenyl ether (20 x weight) and heated to reflux at 269° C. for 45 minutes. After cooling to room temperature, hexane was added in portions and the resulting precipitate was collected by filtration yielding 10.96 g (0.054 mole) of methyl 4-hydroxy-2-quinolinecarboxylate as light yellow crystals having a melting point of 226°-228° C.

EXAMPLE 2

The purpose of this example is to demonstrate the synthesis one of the compounds of Formula I, methyl 4-methoxycarbonylmethyloxy-2-quinolinecarboxylate.

NaH (0.35 g, 0.0073 mole), washed once with 20 ml sieve-dried hexane, was suspended in 20 ml sieve-dried DMF. A suspension of methyl 4-hydroxy-2-quinidinecarboxylate (1.25 g, 0.0061 mole) prepared as in Example 1, in DMF was added in portions and gas evolution noted. After stirring for 20 minutes, methyl bromoacetate (0.75 ml, 0.0079 moles) in 10 ml DMF was added dropwise and the reaction was stirred overnight. It was quenched into sat. NH$_4$Cl and extracted 3x's with a 1:1 mixture of ether:ethyl acetate. The organic layer was washed with H$_2$O and sat. NaCl and dried over MgSO$_4$. Evaporating the solvent gave an off-white solid which was recrystallized from hexane/EtoAC. 1.10 g (65%) of methyl 4-methoxycarbonylmethyloxy-2-quinolinecarboxylate was obtained as white crystals having a melting point of 121°-123° C.

EXAMPLE 3

The purpose of this example is to demonstrate the preparation of a compound of Formula I by
the manipulating the side chains, R$_1$ and R$_2$ of another compound of Formula I.

A sample of methyl 4-methoxycarbonylemethyloxy-2-quinolinecarboxylate (0.20 g, 0.00073 mole) prepared as in Example II, was hydrolyzed by the addition of 1M LiOH (2.2 ml, 0.2233 mole) in H$_2$O/MeOH. After stirring for 18 hours, the MeOH was evaporated, the product dissolved in H$_2$O, and acidified to pH 2.6 with 1N HCl hereby precipitating a white solid. A yield of 0.15 g (83%) of 4-carboxymethyloxy-2-quinolinecarboxylic acid was obtained after filtering and drying in a vacuum dessicator. Melting point was 240° C. (dec.).

The following examples will be used to demonstate the preparation of additional compounds of Formula I.

EXAMPLE 4

4-carboxymethyloxy-6-methyoxy-2-quinoline-carboxcylic acid

Using the methodolgy of examples 1-3, but utilizing p-methyoxyaniline as one of the starting materials, there was obtained the title compound as a white solid having a melting point of 246° C. (dec.).

EXAMPLE 5

4-carboxymethyloxy-6-chloro-2-quinolinecarboxylic acid

Using the methodology of examples 1-3, ut substituting 4-chloroaniline as the starting material, there was obtained the title compound as a white solid having a melting point of 260° C.

EXAMPLE 6

4-carboxymethyloxy-5,7-dichloro-2-quinoline-carboxylic acid

Using the methodology of examples 1-3, but substituting 3,5-dichloroaniline as one of the starting materials there was obtained the title compound as a white solid having a melting point of 227° C. (dec.).

EXAMPLE 7

Methyl 7-cyano-4-methoxycarbonylmethyloxy-2-quinolinecarboxylate and 4-carboxymethyloxy-5-cyano-2-quinolinecarboxylic acid Using the methodology of example 1, but substituting 3-aminobenzonitrile, there was obtained an approximately 1:1 mixture of methyl 5-cyano-4-hydroxy-2-quinolinecarboxylate and methyl 7-cyano-4-hydroxy-2-quinolinecarboxylate. These compounds were not separated but alkylated with methyl bromoacetate as described in example 2 to afford a mixture of compounds which were separated by flash chromatography on silica gel. There was obtained methyl 5-cyano-4-methoxy-carbonylmethyloxy-2-quinolinecarboxylate and methyl 7-cyano-4-methoxycarbonylmethyloxy-2-quinolinecarboxylate having a melting point of 160°-161° C.

Treatment of methyl 5-cyano-4-methoxycarbonyl-metnyloxy-2-quinolinecarboxylate as described above in example 3 afforded 4-carboxymethyloxy-5-cyano-2-quinolinecarboxylic acid having a melting point of 222°-224° C.

EXAMPLE 8

4-(3-carboxypropyloxy)-2-quinolinecarboxylic acid

Using the methodology of examples 1-3, but substituting ethyl 4-bromobutyrate as one of the starting materials, there was obtained the title compounds as a white solid having a melting point of 259° C. (dec.)

EXAMPLE 9

4-carboxymethyloxy-7-chloro-2-quinolinecarboxylic acid and 4-carboxymethyloxy-5-chloro-2-quinoline-carboxylic acid Following the procedure of example 1, but substituting 3-chloroaniline as the starting material there was obtained a mixture of methyl 7-chloro-4-hydroxy-2-quinoline-carboxylate and methyl 5-chloro-4-hydoxy-2-quinoline-carboxylate. The pure compounds were obtained by their differential solubility in acetic acid as described in Heindel, et al., J. Med. Chem. 1968, 11, 1218.

The purified methyl 7-chloro-4-hydroxy-2-quinoline-carboxylate was alkylated with methyl bromoacetate as described in example 2 to produce methyl 7-chloro-4-methoxycarbonylmethyloxy-2-quinolinecarboxylate as a white solid having a melting point of 153.5°-154.5° C.

Treatment of methyl 7-chloro-4-methoxycarbonyl-methyloxy-2-quinolinecarboxylate with LiOH as described in example 3 produced 4-carboxymethyloxy-7-chloro-2-quinolinecarboxylic acid as a white solid having a melting point of 227°-228° C. (dec.).

The purified methyl 5-chloro-4-hydroxy-2-quinolinecarboxylate is alkylated with methyl bromoacetate as described in example 2 to produce methyl 5-chloro-4-methoxycarbonylmethyloxy-2-quinolinecarboxylate.

Treatment of methyl 5-chloro-4-methoxycarbonyl-methyloxy-2-quinolinecarboxylate with LiOH as described in example 3 will produce 4-carboxymethyloxy-5-chloro-2-quinoline-carboxylate.

EXAMPLE 10

4-(2-carboxyethyloxy)-2-quinolinecarboxylic acid

This example demonstrates the synthesis of those compounds of Formula I in which X is O and n is 1.

Methyl 4-hydroxy-2-quinolinecarboxylate (3.45 g, 0.017 m) was suspended in 50 ml t-butanol and then admixed with 1.0 equivalent triethylamine. To the resulting solution was added methyl propiolate (2.40 ml, 0.017 m) and the mixture stirred at RT. After 1.5 hours a solid began to precipitate and the reaction mixture was heated to 50° C. for 2 hours then cooled to RT and stirred at ambient temperature for 16 hours. The reaction was quenched into water. The solid from methanol-water to afford after drying methyl 4-(2-carbonyle-thyleneoxy)-2-quinolinecarboxylate (3.31 g, 0.012 m, 68%), having a melting point of 130.0°-130.8° C.

Methyl 4-(2-methoxycarbonylethyleneoxy)-2-quinoline-carboxylate (1.0 g, 0.0035 m) dissolved in 100 ml of 1:1 ethyl acetate/methanol containing 0.1 g of 10% Pd/C catalyst was hydrogenated at 45 psi for 2.5 hours with constant agitation. The catalyst was removed by filtration and the filtrate evaporated to give a white solid which was purified by flash chromatography on silica gel eluting with 60/40 hexane/ethyl acetate. Methyl 4-(3-methoxycarbonylethyloxy)-2-quinolinecarboxylate was obtained as a white solid (0.41 g, 41%).

Methyl 4-(2-methoxycarbonylethyloxy)-2-quinoline carboxylate (0.41 g, 0.0014 m) was hydrolyzed by the addition of 1M LiOH (3.6 ml, 0.0036 m) in $H_2O$/MeOH. After stirring for 18 hours, the methanol was evaporated, the residue dissolved in $H_2O$, extracted with ethyl acetate, and added to excess aqueous HCl (final pH=1.5). The resulting precipitate was filtered, washed with water and dried to give a white solid containing the desired compound. The solid was suspended in water and dissolved by careful addition of 0.5N NaOH. This solution is purified by application to an anionic ion-exchange resin column and after elution with Hz) and dilute aqueous HCl, 4-(2-carboxyethyloxy)-2-quinolinecarboxylate is obtained.

EXAMPLE 11

4-carboxymethyloxy-7-methoxy-2-quinoline-carboxylic acid

Using the methodology of examples 1-3, but utilizing 3-methoxyaniline as one of the starting materials, there was obtained the title compound as a white solid having a melting point of 259°-261° C. (dec.).

EXAMPLE 12

4-carboxymethyloxy-8-fluoro-2-quinoline-carboxylic acid

Using the methodology of examples 1-3, but utilizing 2-fluoroaniline as one of the starting materials, there was obtained the title compound as a white solid having a melting point of 214°-216° C. (dec.).

EXAMPLE 13

4-carboxymethyloxy-8-chloro-2-quinoline-carboxylic acid

Using the methodology of examples 1-3, but utilizing 2-chloroaniline as one of the starting materials, there was obtained the title compound as an off-white solid having a melting point of 215°-216° C. (dec.).

EXAMPLE 14

4-carboxamidomethyloxy-2-quinolinecarboxamide

4—Carboxymethyloxy-2-quinolinecarboxylic acid from example 3 is treated with excess thionyl chloride at RT until all solids have dissolved and no further gas evolution occurs. The excess thionyl chloride is removed under vacuum and the residue dissolved in THF. Excess concentrated aqueous ammonia is added to the THF solution and stirred for 1 hour. The reactions mixture is quenched into water, made weakly acidic with 0.5 N HCl (pH 3.0), and the resulting solid is filtered. After washing the solid with water and drying, the title compounds is obtained.

EXAMPLE 15 n-propyl 4-propyloxycarbonylmethyloxy-2-quinolinecarboxylate

The purpose of this example is to demonstrate the preparation of a compound of Formula I, n-propyl 4-(1-propyloxycarbonyl)methyloxy-2-quinolinecarboxylate. This example also demonstrates a method by which a compound of Formula I can be prepared in which $R_1$ and $R_2$ are represented by ester side chains.

4—Carboxymethyloxy-2-quinolinecarboxylic acid (0.35 g, 0.0014 m) was dissolved/suspended in acetonitrile containing diisopropylethylamine (5 eq., 0.007 m). Propyl iodide (10 eg.; 1.36 ml) was added at room temperature and the mixture stirred at ambient temperature for 80 hours. The acetonitrile was removed by evaporation and the resultant oil dissolved in diethyl ether. The ethereal solution was washed with 0.1N HCl, water, saturated sodium chloride solution, and then dried over anhydrous magnesium sulfate. The drying agent was removed by filtration and after solvent evaporation at reduced pressure the residue was purified by silica gel flash chromatography. There was obtained 0.37 g (0.0011 m, 80%) of n-propyl 4-(n-propyloxycarbonyl)-methyloxy-2-quinoline-carboxylate.

EXAMPLE 16

4-carboxymethyloxy-2-quinolinecarboxylic acid

The purpose of this example is to demonstrate another method by which 4-carboxymethyloxy-2-quinolinecarboxylic acid may be produced from kynurenic acid, (4-hydroxy-2-quinolinecarboxlic acid), which is commercially available.

NaH (50% in oil, 2.24 g, 0.046 m) was washed 2x with 25 ml portions of sieve-dried hexane, then covered with 35 ml sieve-dried DMF. A suspension of kynurenic acid (4.0 g, 0.021 m) in 45 ml DMF was added in portions. Gas evolution was noted. The suspension was heated to 60° C. for one hour and cooled to RT, after which ethyl bromoacetate (7.0 g, 0.042 mole) in 40 ml DMF was added dropwise. The reaction was stirred at room temperature overnight, then quenched into ice water and extracted 3x's with $Et_2O$. The organic layer was backwashed with $H_2O$ and sat. NaCl and dried over $MgSO_4$. Removal of the drying agent and evaporation of the $Et_2O$ gave a crude oil which was purified by flash chromatography in 65/35 hexane/EtOAc to yield 2.27 g (0.0063 m, 30% yield) of desired ethoxy- carbonyl-methyl 4-ethoxycarbonylmethyloxy-2-quinoline-carboxylate. This material (1.57 g, 0.0043 m) was dissolved in 60 ml EtOH containing 5 ml $H_2O$ and 15 ml 1M LiOH (0.015 m). The mixture was stirred at RT 2.5 hours. The bulk of the EtOH was removed under vacuum, the residue diluted with 30 ml $H_2O$, and the mixture adjusted to pH 2.0 with 1N HCl. The resulting precipitate was filtered, washed with water, and dried to give 4-carboxymethyloxy-2-quinolinecarboxylic acid (0.76 g, 72%) as a white solid, having a melting point of 239°-241° C. (dec.).

EXAMPLE 17

7-hydroxythieno[3,2-b]pyridine-5-carboxylic acid

Using the methodology of example 1, but utilizing 3-aminothiophene as one of the starting materials (Steinkopf, Liebigs, Ann. Chem. 1914, 403, 45), there is obtained methyl 7-hydroxythieno[3,2-b]pyridine-5-carboxylate as the product.

A sample of methyl 7-hydroxythieno[3,2-b]pyridine-5-carboxylate is hydrolyzed by the addition of 2.5 equivalents of aqueous 1M LiOH and stirred for 16 hours at RT. The aqueous reaction mixture is extracted 2x with ethyl acetate and acidified to pH 2.0 with aqueous 1N HCl. The resulting precipitate is filtered, washed with water and dried to afford 7-hydroxythieno[3,2,b-]pyridine-5-carboxylic acid.

EXAMPLE 18

7-carboxymethyloxythieno[3,2-b]pyridine-5-carboxylic acid

Using the methodology of examples 2 and 3, but substituting methyl 7-hydroxythieno[3,2-b]pyridine-5-carboxylate as one of the starting materials will produce 7-carboxymethyloxthieno[3,2-b]pyridine-5-carboxylic acid.

EXAMPLE 19

4-hydroxythieno[2,3,b]pyridine-6-carboxylic acid

Using the methodology of example 1, but utilizing 2-aminothiophene (Klemm, et al., J. Org. Chem., 1969, 34, 347) as one of the starting materials, will produce methyl 4-hydroxythieno[2,3-b]pyridine-6-carboxylate.

A sample of methyl 4-hydroxythieno[2,3-b]pyridine-6-of aqueous 1M LiOH and stirred for 16 hours at RT. The aqueous reaction mixture is extracted 2x with ethyl acetate and acidified to pH 2.0 with aqueous 1N HCl. The resulting precipitate is filtered, washed with water and dried to give 4-hydroxythieno[2,3-b]pyridine-6-carboxylic acid.

EXAMPLE 20

4-carboxymethyloxythieno[2,3-b]pyridine-6-carboxylic acid

Using the methodology of examples 2 and 3, but utilizing methyl 4-hydroxythieno[2,3-b]pyridine-6-carboxylate as one of the starting materials, there is obtained 4-carboxy-methyl-oxythieno[2,3-b]pyridine-6-carboxylic acid.

EXAMPLE 21

Dimethyl 7-hydroxythieno[3,4-b]pyridine-3,5-dicarboxylate

Using the methodology of example 1, but utilizing methyl 3-amino-2-thiophenecarboxylate as one of the starting materials, there is obtained dimethyl 7-hydroxythieneo[3,4-b]pyridine-3,5-dicarboxylate.

EXAMPLE 22

7-carboxymethyloxythieno[3,4-b]pyridine-3,5-dicarboxylic acid

Using the product of example 21 and employing the methodology of examples 2 and 3, there is obtained 7-carboxymethyloxythieno[3,4-b]pyridine-3,5-dicarboxylic acid.

EXAMPLE 23

4-carboxymethyloxy-5,7-difluoro-2-quinoline-carboxylic acid

Using the methodology of examples 1-3, but utilizing 3,5-difluoroaniline as one of the starting materials, there is obtained 4-carboxymethyloxy-5,7-difluoro-2-quinoline-carboxylic acid.

EXAMPLE 24

4-carboxymethylthio-2-quinolinecarboxylic acid

One equivalent of 3-methyl 4-hydroxy-2-quinolinecarboxylate is suspended/dissolved in 25x weight of THF and placed in a cool water (20°-25° C.) bath, to this mixture is added 0.6 equivalents of 2,4-bis(4-methoxyphenyl)-1,3-dithia-2,4-disphosphetane-2,4-disulfide (Lawesson's Reagent) in several portions. The reaction mixture became homogeneous and turned dark red in color. After a short period, a solid begins to precipitate from solution. This solid is methyl 4(1H)-thioquinolone-2-carboxylate.

Using the methodology of examples 2 and 3, but utilizing the methyl 4(1H)-thioquinolone-2-carboxylate produced above as one of the starting materials, there is produced 4-carboxymethylthio-2-quinolinecarboxylate.

EXAMPLE 25

4-(2-carboxymethylthio)quinoline-2-carboxylic acid

Methyl 4(1H)-thioquinolone-2-carboxylate (1.0 equivalent) from example 24 is suspended/dissolved in MeOH containing a catalytic amount of ethyldiisopropylamine. To this mixture is added methyl acrylate (3 equivalent) and the whole is refluxed for 3 hours. The bulk of the solvent is removed under vacuum and the residue is recrystallized from ethyl acetate/ hexane to give methyl 4-(2-methoxycarbonyl-ethylthio)-quinoline-2-carboxylate.

This methyl 4-(2-methoxycarbonylethylthio)quinoline-2-carboxylate is hydrolyzed by the addition of 3 equivalents of aqueous 1M LiOH in MeOH/H2O and stirring at RT. After stirring for 16 hours, the methanol is evaporated, the residue diluted with water and extracted 2x with ethyl acetate. The aqueous layer is acidified to pH 1.5 by the addition of aqueous 1N HCl and the solid obtained is filtered, washed with water, and dried to afford 4-(2-carboxyethylthio)quinoline-2-carboxylic acid.

EXAMPLE 26

4-carboxymethylamino-2-quinolinecarboxylic acid

This Example demonstrates a method by which those compounds of formula I in which X is represented by NH.

According to the procedure of Wright, Synthesis, 1984, 1058, methyl 4-hydroxy-2-quinolinecarboxylate (2.03 g, 0.01 m) and p-toluenesulfonyl isocyanate (1.97 g, 0.01 m) were mixed in reagent grade acetonitrile at RT. The heterogeneous mixture was heated at reflux until the evolution of $CO_2$ had ceased (ca 2-3 hours). During this time a yellow solid formed. After cooling to RT, the yellow solid was collected by filtration, washed with acetonitrile, and dried to give methyl 4-(p-toluenesulfonylimino)-1,4-dihydroquinoline-2-carboxylate (2.93 g, 82%), melting point of 264°-265° C. (dec.), as a yellow solid.

Using the methodology of example 2, but substituting methyl 4-(p-toluenesulfonylimino)-1,4-dihydroquinoline-2-carboxylate as one of the starting materials, there was obtained methyl 4-(N-methoxycarbonylmethyl-N-p-toluene-sulfonyl)amino-2-quinolinecarboxylate as an off white solid having a melting point of 186°-189° C.

Methyl 4-(N-methoxycarbonylmethyl-N-p-toluenesulfonyl)amino-2-quinoline carboxylate (1 part) was added to 90% $H_2SO_4$ (7 parts) at 0° with good stirring. After the mixture became homogeneous, it was stirred for 1 hour at 0° and then let warm to RT and stirred for 2 hours. The reaction mixture was poured onto ice and the resulting aqueous mixture was carefully adjusted to pH 3.5 with the addition of 50% NaOH followed by 1N NaOH. The precipitate which formed was filtered, washed with cold water, and dried to afford 4-carboxymethylamino-2-quinolinecarboxylic acid as a white solid having a melting point of 260°-261° C.

EXAMPLE 27

Carboxymethyloxy-7-fluoro-2-quinolinecarboxylic acid

Using the methodology of example 1 but utilizing 3-fluoroaniline as one of the starting materials, there was obtained a mixture of methyl 5-fluoro-4-hydroxy-2-quinolinecarboxylate and methyl 7-fluoro-4-hydroxy-2-quinolinecarboxylate as product. The pure 7-fluoro isomer was obtained by two recrystallizations from methanol.

Using the methodology of examples 2 and 3 but utilizing the purified methyl 7-fluoro-4-hydroxy-2-quinolinecarboxylate as one of the starting materials there was obtained Carboxymethyloxy-7-fluoro-2-quinolinecarboxylic acid as a white solid having a melting point of 251°-253° C. dec.

EXAMPLE 28

2-(Dimethylamino)ethyl 5,7-dichloro-4-[2-(dimethylamino)ethyloxycarbonyl]-methyloxy-2-quinolinecarboxylate 4—Carboxymethyloxy-5,7-dichloro-2-quinolinecarboxylic acid from example 6 is treated with excess thionyl chloride at RT until all solids have dissolved and no further gas evolution occurs. The excess thionyl chloride is removed under vacuum and the residue dissolved in reagent THF. This suspension/solution is cooled to about 0° C. and excess dimethylaminoethanol is added dropwise with good stirring. The reaction is allowed to warm to RT and stirred for 16 hours. The reaction mixture is quenched into cold 5% sodium bicarbonate solution and extracted several times with ethyl acetate. The organic extracts are combined, washed successively with water, saturated NaCl solution and dried over magnesium sulfate. Removal of the drying agent by filtration and evaporation of the ethyl acetate will afford 2-(dimethylamino)ethyl 5,7-dichloro-4-[2-(dimethylamino) ethyloxycarbonyl]methyloxy-2-quinolinecarboxylate

EXAMPLE 29

4-Carboxymethylamino-5,7-dichloro-2-quinolinecarboxylic acid

Using the methodology of example 26 but substituting methyl 5,7-dichloro-4-hydroxy-2-quinolinecarboxylate from example 6 there was obtained methyl 5,7-dichloro-4-(p-toluenesulfonylimino)-1,4-dihydroquinoline-2-carboxylate as a yellow solid having melting point of 210°-212° C.

Using the methodology of example 2, but substituting this methyl 5,7-dichloro-4-(p-toluenesulfonylimino)-1,4-dihydroquinoline-2-carboxylate as one of the starting materials there was obtained methyl 5,7-dichloro-4-(N-methoxycarbonylmethyl-N-p-toluenesulfonyl)amino-2-quinolinecarboxylate as a solid of melting point 159°-161° C.

Using the methodology of example 3 but substituting methyl 5,7-dichloro-4-(N-methoxycarboxylmethyl-N-toluenesulfonyl)amino-2-quinolinecarboxylate there was obtained 5,7-dichloro-4-(N-carboxymethyl-N-p-toluene-sulfonyl)amino-2-quinolinecarboxylic acid as a solid which was added to 7-10 parts 90% $H_2SO_4$ at 0° with efficient stirring. After the mixture became homogeneous the stirring was continued for each hour while the solution warmed to room temperature. The reaction mixture was then poured onto ice and the resulting cold aqueous mixture was carefully adjusted to pH 3.0-3.5 by the addition of 1 N NaOH. The off-white precipitate which formed was filtered, washed several times with cold water and dried to give 4-carboxymethylamino-5,7-dichloro-2-quinolinecarboxylic acid having a melting point of 265°-270° C. (dec.).

EXAMPLE 30

4—Carbomethyloxy-6-trifluoromethyl-2-quinoline-carboxylic acid

Using the methodology of examples 1-3, but substituting 4-aminobenzotrifluoride as one of the starting materials there was obtained the title compound as a white solid having a melting point of 225°-227° C. (dec.).

EXAMPLE 31

4—Carboxymethyloxy-8-fluoro-2-quinoline-carboxylic acid

Using the methodology of examples 1-3, but substituting 2-fluoroaniline as one of the starting materials, there was obtained the title compound as a white solid having a melting point of 214°-216° C. (dec.).

EXAMPLE 32

4—Carboxymethyloxy-6,7-dichloro-2-quinoline-carboxylic acid and 4-carboxymethyloxy-5,6-dichloro-2-quinlinecarboxylic acid.

Using the methodology of example 1, but substituting 3,4-dichloroaniline there was obtained an approximately 1:1 mixture of methyl 6,7-dichloro-4-hydroxy-2-quinoline-carboxylate and methyl 5,6-dichloro-4-hydroxy-2-quinoline-carboxylate. These compounds were not separated but alkylated with methyl bromoacetate as described in example 2 to afford a mixture of compounds which were separated by flash chromatography on silica gel using mixtures of ethyl acetate and hexane as eluent. There was obtained methyl 6,7-dichloro-4-methaoxycarbonylmethyloxy-2-quinoline-carboxylate (mp 190°-192° C.).

Treatment of the purified methyl 6,7-dichloro-4-methoxycarbonylmethyloxy-2-quinolinecarboxylate as described in example 3 afforded 4-carboxymethyloxy-6,7-dichloro-2-quinolinecarboxylic acid as a solid of melting point 248°250° C. (dec.).

What is claimed is:

1. A compound of the formulae:

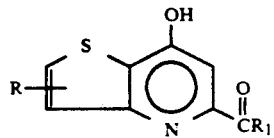

Formula II

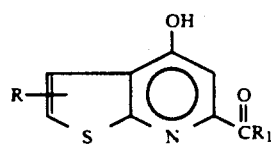

Formula III

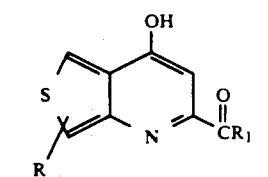

Formula IV in which $R_1$ is represented by a substituent selected from the group consisting of —$NR_3R_4$, —OH, —$OR_5$, —$OCH_2OCOR_6$ and, —O—$(CH_2)p$ $NR_7R_8$, in which p is an integer from 1-4; $R_3$ and $R_4$ are each independently represented by hydrogen or a $C_{1-6}$ alkyl; $R_5$ nd $R_6$ are each independently represented by $C_{1-6}$ alkyl, phenyl, substituted phenyl, or an alkylphenyl substituent in which the phenyl ring may be optionally substituted; $R_7$ and $R_8$ are independently represented by a $C_{1-6}$ alkyl or together with the adjacent nitrogen atom form a piperidino, morpholino, or pyrrolidinyl group;

R, which is optionally present, represents 1 or 2 substituents selected from the group consisting of OH, halogen, CN, $NO_2$, $C_{1-6}$ alkyl, $C_{1-6}$ alkoxy, $CF_3$, $OCF_3$, $COOR_3$, and $CONR_3R_4$ in which $R_3$ and $R_4$ are each independently as defined above; the pharmaceutically acceptable acid addition salts thereof and the pharmaceutically acceptable basic additional salts thereof; with the proviso than in the compounds of Formula IV, R is not $COOR_3$.

2. A method for antagonizing the effects of excitatory amino acids upon he NMDA receptor complex comprising administering to a patient in need thereof an antagonistic amount of a compound according to claim 1.

3. A method for the treatment of epilepsy comprising administering to a patient in need thereof an anti-epileptic amount of a compound according to claim 1.

4. A method or the treatment of neurodegenerative diseases comprising administering to a patient in need thereof an effective amount o a compound according to claim 1.

5. A method for preventing ischemic/hypoxic damage to cerebral tissue comprising administering to a patient in need thereof an effective amount of a compound according to claim 1.

6. A method for the treatment of anxiety comprising administering to a patient in need thereof an anxiolytic amount of a compound according to claim 1.

7. A method for producing an analgesic effect comprising administering to a patient in need thereof an analgesic amount of a compound according to claim 1.

8. A pharmaceutical composition according to claim 1 comprising a compound according to claim 1 present in an effective amount in admixture with a pharmaceutically acceptable carrier.

* * * * *